United States Patent
Wood

(10) Patent No.: US 6,495,728 B2
(45) Date of Patent: Dec. 17, 2002

(54) PROCESS AND INTERMEDIATE COMPOUNDS FOR THE PREPARATION OF PESTICIDAL FLUOROOLEFIN COMPOUNDS

(75) Inventor: William Wakefield Wood, Pennington, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/950,905

(22) Filed: Sep. 12, 2001

(65) Prior Publication Data

US 2002/0062049 A1 May 23, 2002

Related U.S. Application Data

(60) Provisional application No. 60/231,995, filed on Sep. 12, 2000.

(51) Int. Cl.$^7$ .................................................. C07C 41/06
(52) U.S. Cl. ...................... 568/635; 568/639; 570/128; 570/204; 585/436
(58) Field of Search ................................ 568/635, 639; 570/128, 204; 585/436

(56) References Cited

U.S. PATENT DOCUMENTS 5,849,958 A * 12/1998 Barnes et al. ............... 558/384
6,262,319 B1 * 7/2001 Barnes et al.

FOREIGN PATENT DOCUMENTS

GB          2288803 A  * 11/1995 .......... C07C/43/225

* cited by examiner

*Primary Examiner*—Rosalynd Keys
(74) *Attorney, Agent, or Firm*—Keil & Weinkauf

(57) ABSTRACT

A two-step process for the preparation of fluoroolefin compounds of formula I

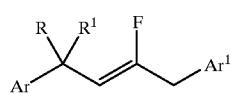

wherein R is hydrogen or alkyl, and $R^1$ is alkyl or cyclopropyl, or R and $R^1$ are taken together with the carbon atom to which they are attached to form a cyclopropyl group;

Ar is phenyl or naphthyl both of which are optionally substituted;
  $Ar^1$ is phenoxyphenyl, biphenyl, phenyl, benzylphenyl, or benzoylphenyl, all of which may be optionally substituted, comprising reacting fluorobromoolefin compounds of formula II

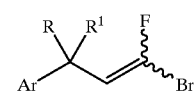

with organozinc compounds of formula III or IV

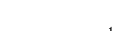

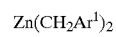

in the presence of a palladium catalyst and a solvent, which compounds of formula II are obtained by reacting aldehyde compounds of formula V

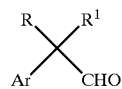

with (a) fluorotribromomethane, (b) a tri(substituted)phosphine or a hexaalkylphosphoramide or a mixture thereof, and (c) zinc, in the presence of a solvent, compounds of formula II.

8 Claims, No Drawings

PROCESS AND INTERMEDIATE COMPOUNDS FOR THE PREPARATION OF PESTICIDAL FLUOROOLEFIN COMPOUNDS

This application claims the benefit under 35 USC 119(e) of provisional application 60/231,995 filed Sep. 12, 2000.

The present invention provides a two-step process for the preparation of pesticidal fluoroolefin compounds of formula I

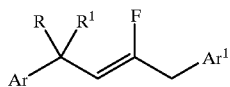

wherein
R is hydrogen or $C_1$–$C_4$-alkyl, and
$R^1$ is $C_1$–$C_4$-alkyl or cyclopropyl, or
R and $R^1$ are taken together with the carbon atom to which they are attached to form a cyclopropyl group;
Ar is phenyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, or
1- or 2-naphthyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups;
$Ar^1$ is phenoxyphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
biphenyl which is unsubstituted or substituted with any combination of from one to five halogen, $C_1$–$C_4$-alkyl, $C_1$–$C_4$-haloalkyl, $C_1$–C4-alkoxy Or $C_1$–$C_4$-haloalkoxy groups,
phenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
benzylphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups, or
benzoylphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
which comprises reacting fluorobromoolefin compounds of formula II

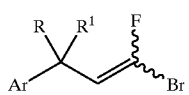

wherein Ar, R and $R^1$ are as described above, with organozinc compounds of formula III or IV

$BrZnCH_2Ar^1$

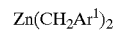

$Zn(CH_2Ar^1)_2$ wherein $Ar^1$ is as described above, in the presence of a palladium catalyst and a solvent,
which compounds of formula II are obtained by reacting aldehyde compounds of formula V

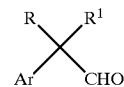

wherein Ar, R and $R^1$ are as defined above, with
(a) fluorotribromomethane,
(b) a tri(substituted)phosphine or a hexaalkylphosphoramide or a mixture thereof, and
(c) zinc,
in the presence of a solvent.

In compounds of formula I, the configuration of the groups $ArCRR^1$- and —$CH_2Ar^1$ about the double bond is preferably predominately mutually trans. "Predominately trans" means that the trans-compound is present at a percentage of at least 80%, preferably above 95%.

The present invention also relates to the fluorobromoolefin compounds of formula II.

Pesticidal fluoroolefin compounds and processes for their preparation are described in WO 94/06741 and GB-A 2 288 803.

However, those processes are not entirely statisfactory because the fluoroolefin compounds are produced in relatively low yields from multi-step processes.

It was therefore an object of the present invention to provide an improved process for the preparation of fluoroolefin compounds.

Accordingly, a two-step overall process for the preparation of fluoroolefin compounds of formula I starting form aldehyde compounds of formula V, via intermediate compounds of formula II, has been found.

Furthermore, compounds of formula II have been found.

Advantageously, the inventive process affords compounds of formula I which are predominately in the trans-configuration.

WO 94/06741 and GB-A 2 288 803 disclose that fluoroolefin compounds are obtained in four steps starting from aldehyde compounds of formula V.

Exemplary of halogen hereinabove are fluorine, chlorine, bromine and iodine;

The term "alkyl" is defined as a saturated, straight or branched chain hydrocarbon with 1 to 4 carbon atoms, such as methyl, ethyl, propyl, 1-methyl-ethyl, butyl, 1-methyl-propyl, 2-methyl-propyl and 1,1-dimethyl-propyl.

The term "alkoxy" is defined as a saturated, straight or branched chain hydrocarbon with 1 to 4 carbon atoms (as described above) which is bond to the backbone via an oxygen (—O—) atom;

The term "haloalkyl" is defined as an alkyl group, as defined above, wherein the hydrogen atoms may be partially or totally substituted with halogen atoms as defined above, wherein the halogen atoms may be the same or different, for example $C_1$–$C_2$-haloalkyl such as chloro-methyl, bromomethyl, dichloro-methyl, trichloro-methyl, fluoromethyl, difluoro-methyl, trifluoro-methyl, chloro-fluoromethyl, dichlorofluoro-methyl, chloro-difluoro-methyl, 1-chloro-ethyl, 1-bromo- ethyl, 1-fluoro-ethyl, 2-fluoroethyl, 2,2-difluoro-ethyl, 2,2,2-trifluoro-ethyl, 2-chloro-2-fluoro-ethyl, 2-chloro-2,2-difluoro-ethyl, 2,2-dichloro-2-fluoro-ethyl, 2,2,2-trichloro-ethyl and pentafluoro-ethyl, wherein the halogen atoms may be the same or different.

The term "haloalkoxy" is defined as an alkoxy group as defined above, wherein the hydrogen atoms may be partially or totally substituted with one or more halogen atoms as defined above, wherein the halogen atoms may be the same or different.

Wavy lines in structural formulae depict the carbon—carbon double bond in both the E- or the Z- isomeric configuration.

Groups containing two or more rings, such as phenoxyphenyl, biphenyl, benzylphenyl and benzoylphenyl, which may be substituted, may be substituted on either ring unless otherwise specified herein.

In a preferred embodiment of the present invention, a fluorobromoolefin of formula II is reacted with at least one molar equivalent, such as 1 to 2 molar equivalents, of an organozinc compound of formula III or IV, and 0,001 to 0,2, preferably 0,01 to 0,1 molar equivalent of a palladium catalyst in the presence of a solvent, preferably in a temperature range of −70° C. to 70° C.

The product compounds of formula I may be isolated by diluting the reaction mixture with water and extracting the product with a suitable extraction solvent. In the isolation procedure, conventional extraction solvents such as ether, ethyl acetate, toluene, and dichloromethane may be utilized.

Preferred palladium catalysts for use in the present invention include, but are not limited to, bis(dibenzylideneacetone)palladium(O), tetrakis(triphenylphosphine)palladium(O), bis(acetonitrile)palladium(II) chloride, bis(triphenylphosphine)palladium(II) chloride, [1,4-bis (diphenylphosphine)butane]palladium(II) dichloride, [1,1'-bis(diphenylphosphino)ferrocene]palladium(II) diacetate, palladium(II) acetate, palladium(II) chloride and mixtures thereof.

Preferred solvents for use in the preparation of compounds of formula I include, but are not limited to, aromatic hydrocarbons such as toluene, benzene, xylenes and mesitylene, halogenated aromatic hydrocarbons such as chlorobenzene and fluorobenzene, carboxylic acid amides, such as N,N-dimethylformamide, ethers such as tetrahydrofuran and dioxane, and halogenated hydrocarbons such as chloroform and carbon tetrachloride, and mixtures thereof.

Preferred solvents for use in the preparation of compounds of formula I include carboxylic acid amides and ethers and mixtures thereof, preferably N,N-dimethylformamide and tetrahydrofuran and mixtures thereof.

In a preferred embodiment of the present invention for the preparation of fluorobromoolefin compounds of formula II, aldehyde compounds of formula V are reacted with at least one molar equivalent, such as 2 to 6 molar equivalents, of fluorotribromomethane, and at least one molar equivalent, such as 2 to 7 molar equivalents, of a tri(substituted) phosphine, and at least one molar equivalent, such as 1 to 4 molar equivalents, of zinc, preferably zinc dust, in the presence of a solvent, preferably in a temperature range of −20° C. to 70° C.

Preferred tri(substituted)phosphines for use in this invention include, but are not limited to, triaryl-phosphines such as tri-phenylphosphine or tri-p-tolyl-phosphine, and tri(branched $C_3$–$C_6$-alkyl)-phosphines such as triisopropylphosphine or triter-tiarybutylphosphine, and mixtures thereof.

Preferred tri(substituted)phosphines which produce compounds of formula II with a preferred ratio of (E):(Z)-isomer include tri-isopropylphosphine and tritertiarybutylphosphine. Preferred ratios of (E):(Z)-isomer of formula II are ratios above 1,5:1, preferably above 2,5:1, more preferably above 3,5;1 (E):(Z).

Preferred hexaalkylphosphoramides for use in the present invention include hexamethylphosphoramide or hexaethylphosphoramide, and mixtures thereof.

Preferred solvents for use in the preparation of fluorobromoolefins of formula II include, but are not limited to, ethers such as diethyl ether or tetrahydrofuran and halogenated hydrocarbons such as dichloromethane, and mixtures thereof.

More preferred solvents for use in the preparation of fluorobromoolefins of formula II include diethyl ether, tetrahydrofuran and dichloromethane, and mixtures thereof.

Starting organozinc compounds of formulae III and IV may be prepared by reacting a bromide compound of formula VI

                              VI wherein $Ar^1$ is described above, with activated zinc (e.g., Rieke zinc) in the presence of a solvent such as tetrahydrofuran.

Aldehyde compounds of formula V may be prepared using conventional procedures known in the art, see for example: Bioorg. Med. Chem. Lett. (1998), 8(3), p. 301; Chem. Pharm. Bull. (1996), 44(10), p. 1858; Tetrahedron Lett. (1996), 37(5), 2629; J. Org. Chem. Soc. (1995), 60 (18), p. 5803; and J. Am. Chem. Soc. (1993), 115, p. 3030.

Preferred fluoroolefin compounds of formula I which may be prepared by the process of the present invention are those wherein the variables have the following meanings, each alone or in combination:

Preferred are compounds of formula I wherein R is hydrogen and $R^1$ is isopropyl or cyclopropyl;

Also preferred are compounds of formula I wherein R and $R^1$ are methyl;

Furthermore, preferred are compounds of formula I wherein R and $R^1$ are taken together with the carbon atom to which they are attached to form a cyclopropyl group.

Preferred are compounds of formula I wherein Ar is phenyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups.

More preferred are compounds of formula I wherein Ar is phenyl which is unsubstituted or substituted with any combination of from one to three halogen, preferably chlorine of fluorine.

Most preferred are compounds of formula I wherein Ar is 4-chlorophenyl.

Moreover, compounds of formula I are preferred wherein $Ar^1$ is 3-phenoxyphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups, 3-biphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups, or phenyl which is unsubstituted or substituted with any combination of from one to five halogen, $C_1$–$C_4$-alkyl, $C_1$–$C_4$-halo-alkyl, $C_1$–$C_4$-alkoxy or $C_1$–$C_4$-haloalkoxy groups.

More preferred are compounds of formula I wherein $Ar^1$ is 3-phenoxy-phenyl which is unsubstituted or substituted with any combination of from one to five halogen, $C_1$–$C_4$-alkyl, $C_1$–$C_4$-halo-alkyl, $C_1$–$C_4$-alkoxy or $C_1$–$C_4$-haloalkoxy groups.

Especially preferred are compounds of formula I wherein $Ar^1$ is 3-phenoxyphenyl which is unsubstituted or substituted with any combination of from one to six halogen, preferably fluorine.

Most preferred compounds of formula I agents are those wherein

R is hydrogen and $R^1$ is isopropyl or cyclopropyl, or R and $R^1$ are methyl, or R and $R^1$ are taken together with the carbon atom to which they are attached to form a cyclopropyl group; and Ar is phenyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups; and $Ar^1$ is 3-phenoxyphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups.

Preferred fluorobromoolefin compounds of formula II are those wherein R, $R^1$ and Ar are as defined above for preferred compounds of formula I.

In a preferred embodiment of this invention, compounds of formula II are in the (E)- configuration.

Preferred compounds of formulae III, IV and V for use in the inventive process are those wherein the variables Ar, R, and $R^1$, respectively, are as defined above for preferred compounds of formula I.

EXAMPLE 1

Preparation of (Z)-1-(p-Tolyl)-1-[2-fluoro-3-(3-phenoxyphenyl)-1-propenyl]cyclopropane,

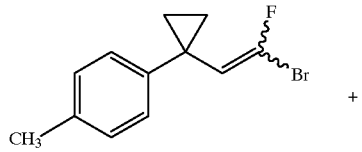

+

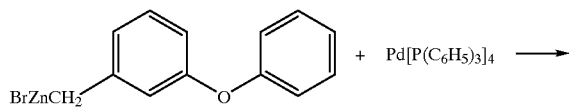

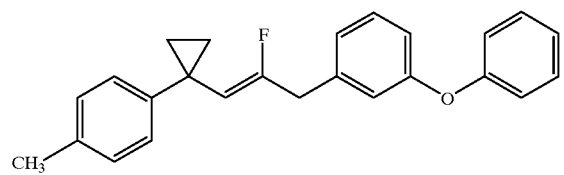

Under a nitrogen atmosphere, a mixture of 1-(2-bromo-2-fluoroethene)-1-(p-tolyl)cyclopropane, (E)- to (Z)- ratio 5:3 (0,5 g, 2 mmol), tetrakis(triphenylphosphine)-palladium (O) (0,2 g, 0,2 mmol), and tetrahydrofuran (20 ml) was treated with a 3-phenoxybenzylzinc bromide solution (prepared from 3-phenoxybenzylbromide (1,1 g, 4 mmol) and Rieke zinc (3,25 ml of a 1,5 molar solution in tetrahydrofuran), and tetrahydrofuran 20 ml). The resultant reaction mixture was stirred at room temperature until the reaction was complete as followed by gas chromatography analysis, diluted with water, and extracted with ethyl acetate. The organic extract was dried over anhydrous magnesium sulfate, and concentrated in vacuo to obtain a residue. Column chromatography of the residue using silica gel and heptane gave the title product (0,18 g) predominately in the (Z)- configuration.

Using essentially the same procedure, the following compounds are obtained predominately in the (Z)- configuration:

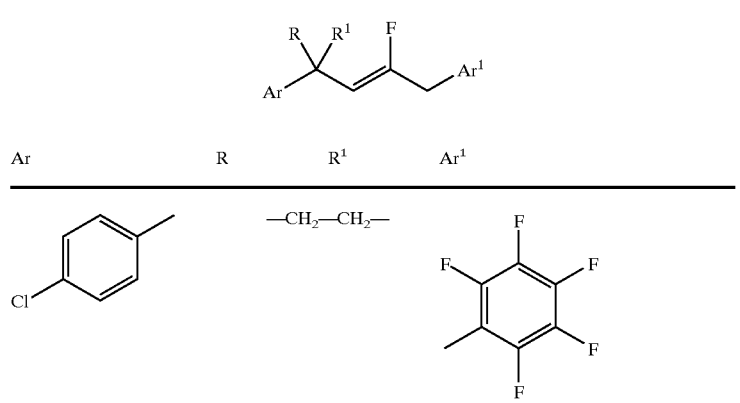

-continued

| Ar | R | R¹ | Ar¹ |
|---|---|---|---|
| 4-Cl-C₆H₄- | CH₃ | CH₃ | pentafluorophenyl |
| 4-CH₃-C₆H₄- | —CH₂—CH₂— | | 3-phenoxyphenyl |
| 4-Cl-C₆H₄- | CH₃ | CH₃ | 2-methyl-biphenyl-3-yl |
| 4-Cl-C₆H₄- | CH(CH₃)₂ | H | 2-methyl-biphenyl-3-yl |
| 4-Cl-C₆H₄- | CH₃ | CH₃ | 4-methyl-2-phenoxy-fluorophenyl |

EXAMPLE 2

Preparation of (Z)-4-(p-Chlorophenyl)-2-fluoro-5-methyl-1-(3-phenoxyphenyl)-2-hexene,

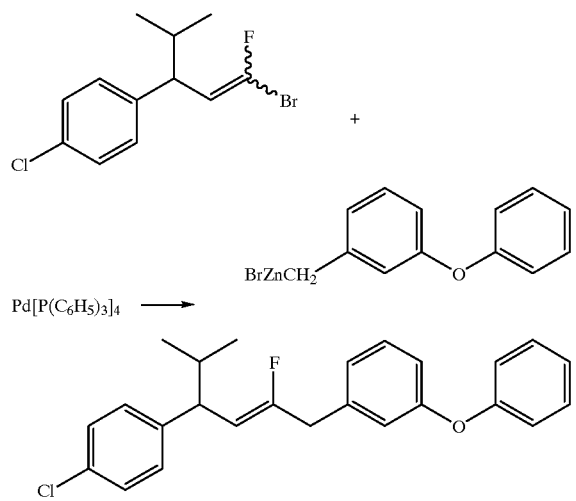

Under a nitrogen atmosphere, a mixture of 1-bromo-3-(p-chlorophenyl)-1-fluoro-4-methyl-1-pentene, (E)- and (Z)- (0,9 g, 3,1 mmol), tetrakis(triphenylphosphine)-palladium(O) (0,25 g, 0,22 mmol), and N,N-dimethyl-formamide (20 ml) was treated with 5 ml of a 3-phenoxybenzylzinc bromide solution (prepared from 3-phenoxybenzyl bromide (1,3 g, 5,4 mmol) and Rieke zinc (4 ml of a 1,5 molar solution in tetrahydrofuran), and tetrahydrofuran 20 ml). The resultant reaction mixture was stirred at room temperature for one hour, treated with an additional 5 ml of the 3-phenoxybenzylzinc bromide solution, stirred at room temperature, and poured into 2 N hydrochloric acid solution. The resultant aqueous mixture was extracted with diethyl ether. The organic extract was dried over anhydrous magnesium sulfate, and concentrated in vacuo to obtain a residue. Column chromatography of the residue using silica gel, and 100:1 and 200:1 hexane/ethyl acetate solutions gave the title product (0,35 g) predominately in the (Z)-configuration.

Following essentially the same procedure, but using the appropriate palladium catalyst, the following compounds are obtained predominately in the (Z)-configuration:

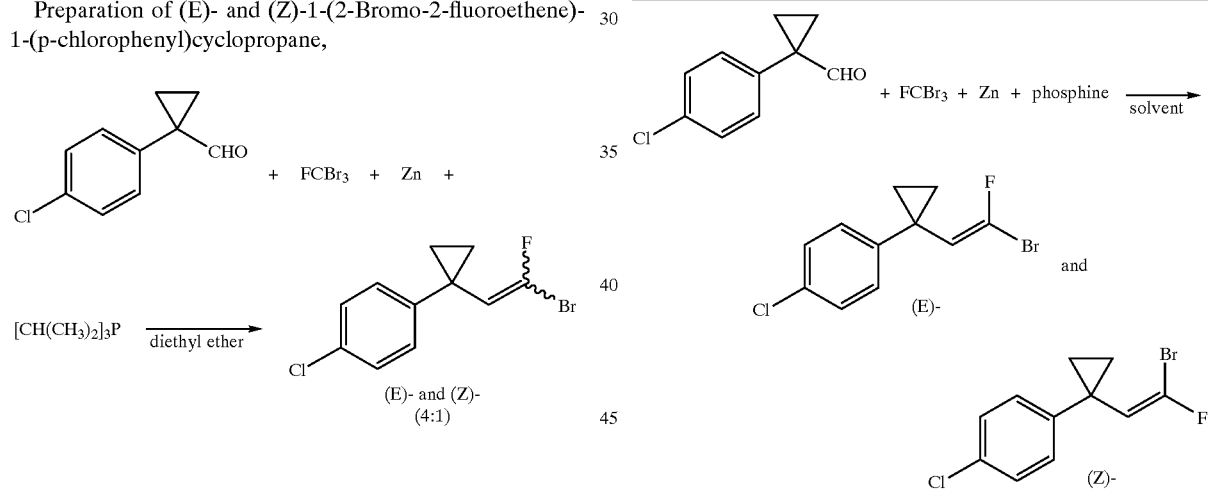

EXAMPLE 3

Preparation of (E)- and (Z)-1-(2-Bromo-2-fluoroethene)-1-(p-chlorophenyl)cyclopropane, A mixture of 1-carboxaldehyde-1-(p-chlorophenyl)-cyclopropane (0,2 g, 1,1 mmol), fluorotribromomethane (0,39 ml, 1,08 g, 4,0 mmol), zinc dust (0,12 g, 1,8 mmol), triisopropylphosphine (0,75 ml, 3,9 mmol), and diethyl ether (20 ml) was stirred at room temperature for one hour, treated with additional triisopropylphosphine (0,3 ml, 1,6 mmol) to give the title product having an (E)- to (Z)- isomer ratio of 4:1. This reaction is listed as reaction no. 1 in Table I.

Following essentially the same procedure, but varying the phosphine and solvent, 1-(2-bromo-2-fluoroethene)-1-(p-chlorophenyl)cyclopropane, (E)- and (Z)- is obtained in the ratios shown below in Table I.

As can be seen from the data in Table I, the (E)- isomer of 1-(2-bromo-2-fluoroethene)-1-(p-chlorophenyl) cyclopropane is obtained in significantly greater amounts relative to the (Z)-isomer when the phosphine is triisopropylphosphine or tritertiarybutylphosphine.

TABLE I

| Reaction No. | Phosphine | Solvent | Product Ratio (E:Z) |
|---|---|---|---|
| 1 | [CH(CH$_3$)$_2$]$_3$P | diethyl ether | 4:1 |
| 2 | [(CH$_2$)$_3$CH$_3$]$_3$P | diethyl ether | No Reaction |
| 3 | (C$_6$H$_5$)$_3$P | diethyl ether | No Reaction |
| 4 | [CH(CH$_3$)$_2$]$_3$P | dichloromethane | 1.7:1 |
| 5 | [C(CH$_3$)$_3$]$_3$P | dichloromethane | 2:1 |
| 6 | (C$_2$H$_5$)$_3$P | dichloromethane | No Reaction |
| 7 | (CH$_3$)$_3$P | dichloromethane | No Reaction |
| 8 | (C$_6$H$_5$)$_3$P | dichloromethane | 1:1.4 |
| 9 | [CH(CH$_3$)$_2$]$_3$P | tetrahydrofuran | 2.5:1 |
| 10 | [(CH$_2$)$_3$CH$_3$]$_3$P | tetrahydrofuran | No Reaction |
| 11 | (CH$_3$)$_3$P | tetrahydrofuran | No Reaction |
| 12 | (C$_6$H$_5$)$_3$P | tetrahydrofuran | 1:1 |

EXAMPLE 4

Preparation of (E)- and (Z)-1-(2-Bromo-2-fluoroethene)-1-(p-to-lyl)cyclopropane,

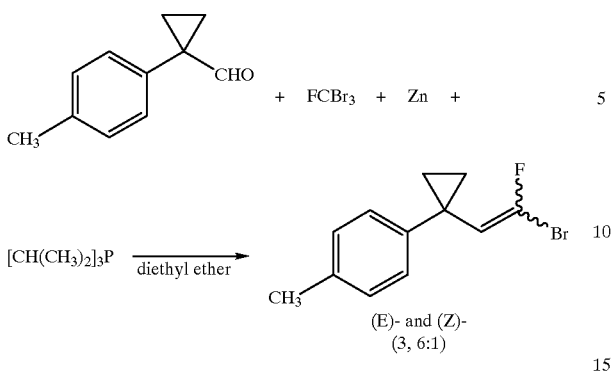

(E)- and (Z)-
(3, 6:1)

Following essentially the same procedure as described in Example 3, but using the reactants shown above, the title product is obtained having an (E)- to (Z)- isomer ratio of 3,6:1.

EXAMPLE 5

Following essentially the same procedure as described in Example 3, the following compounds are obtained:

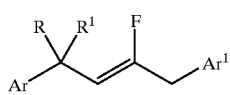

| W | R | R$^1$ | Phosphine | Solvent | Product Ratio (E:Z) |
|---|---|---|---|---|---|
| Cl | CH(CH$_3$)$_2$ | H | (C$_6$H$_5$)$_3$P | dichloromethane | 2:1 |
| F | CH$_3$ | CH$_3$ | (C$_6$H$_5$)$_3$P | tetrahydrofuran | 2:1 |
| F | —CH$_2$—CH$_2$— | | (C$_6$H$_5$)$_3$P | tetrahydrofuran | 1:1 |
| Cl | CH$_3$ | CH$_3$ | (C$_6$H$_5$)$_3$P | dichloromethane | 1:1.3 |

What is claimed is:

1. A two-step process for the preparation of fluoroolefin compounds of formula I

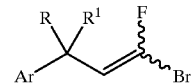

wherein
R is hydrogen or C$_1$–C$_4$-alkyl, and
R$^1$ is C$_1$–C$_4$-alkyl or cyclopropyl, or
R and R$^1$ are taken together with the carbon atom to which they are attached to form a cyclopropyl group;
Ar is phenyl which is unsubstituted or substituted with any combination of from one to three halogen, C$_1$–C$_4$-alkyl, C$_1$–C$_4$-haloalkyl, C$_1$–C$_4$-alkoxy or C$_1$–C$_4$-haloalkoxy groups, or
1- or 2-naphthyl which is unsubstituted or substituted with any combination of from one to three halogen, C$_1$–C$_4$-alkyl, C$_1$–C$_4$-haloalkyl, C$_1$–C$_4$-alkoxy or C$_1$–C$_4$-haloalkoxy groups;
Ar$^1$ is phenoxyphenyl which is unsubstituted or substituted with any combination of from one to five halogen, C$_1$–C$_4$-alkyl, C$_1$–C$_4$-haloalkyl, C$_1$–C$_4$-alkoxy or C$_1$–C$_4$-halo- alkoxy groups, biphenyl which is unsubstituted or substituted with any combination of from one to five halogen, C$_1$–C$_4$-alkyl, C$_1$–C$_4$-haloalkyl, C$_1$–C$_4$-alkoxy or C$_1$–C$_4$-haloalkoxy groups, phenyl which is unsubstituted or substituted with any combination of from one to five halogen, C$_1$–C$_4$-alkyl, C$_1$–C$_4$-haloalkyl, C$_1$–C$_4$-alkoxy or C$_1$–C$_4$-haloalkoxy groups, benzylphenyl which is unsubstituted or substituted with any combination of from one to five halogen, C$_1$–C$_4$-alkyl, C$_1$–C$_4$-haloalkyl, C$_1$–C$_4$-alkoxy or C$_1$–C$_4$-haloalkoxy groups, or benzoylphenyl which is unsubstituted or substituted with any combination of from one to five halogen, C$_1$–C$_4$-alkyl, C$_1$–C$_4$-haloalkyl, C$_1$–C$_4$-alkoxy or C$_1$–C$_4$-haloalkoxy groups, which comprises reacting fluorobromoolefin compounds of formula II

wherein Ar, R and R$^1$ are as described above, with organozinc compounds of formula III or IV

wherein Ar$^1$ is as described above, in the presence of a palladium catalyst and a solvent,
which compounds of formula II are obtained by reacting aldehyde compounds of formula V

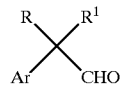

wherein Ar, R and R$^1$ are as defined above, with
(a) fluorotribromomethane,
(b) a tri(substituted)phosphine or a hexaalkylphosphoramide or a mixture thereof, and
(c) zinc,
in the presence of a solvent.

2. The process according to claim 1 wherein the palladium catalyst is selected from the group consisting of bis(dibenzylideneacetone)palladium(O), tetrakis(triphenylphosphine)palladium(O), bis(acetonitrile)palladium(II) chloride, bis(triphenylphosphine)palladium(II) chloride, [1,4-bis(di-phenylphosphine)butane]palladium(II) dichloride, [1,1'-bis(diphenylphosphino)ferrocene]palladium(II) diacetate, palladium(II) acetate and palladium(II) chloride, and mixtures thereof.

3. The process according to claim 1 wherein the palladium catalyst is present in an amount of 0.001 to 0.2 molar equivalent relative to the compound of formula II.

4. The process according to claim 1 wherein the phosphine is selected from the group consisting of triphenylphosphine tri-(p-tolyl)phosphine and a tri- (branched C$_3$–C$_6$-alkyl)phosphine and mixtures thereof; and the hexaalkylphosphoramide is selected from the group consisting of hexamethylphosphoramide and hexaethylphosphoramide and mixtures thereof.

5. The process according to claim 1 wherein fluorotribromomethane is present at 2 to 6 molar equivalents related to compounds of formula V.

6. The process according to claim 1 wherein the tri(substituted)phosphine is present at 2 to 7 molar equivalents related to compounds of formula V.

7. The process according to claim 1 wherein zinc is present at 1 to 4 molar equivalents related to compounds of formula V.

8. The process according to claim 1 wherein R is hydrogen and $R^1$ is isopropyl or cyclopropyl, or R and $R^1$ are methyl, or R and $R^1$ are taken together with the carbon atom to which they are attached to form a cyclopentyl group; Ar is phenyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups; and $Ar^1$ is 3-phenoxyphenyl which is unsubstituted or substituted with any combination of from one to five halogen, $C_1$–$C_4$-alkyl, $C_1$–$C_4$-haloalkyl, $C_1$–$C_4$-haloalkoxy groups.

\* \* \* \* \*